(12) United States Patent
Thorn et al.

(10) Patent No.: US 10,111,973 B2
(45) Date of Patent: Oct. 30, 2018

(54) METHOD AND SYSTEM FOR CLEANING AND SANITIZING CONVEY LINES

(71) Applicant: SCHENCK PROCESS LLC, Kansas City, MO (US)

(72) Inventors: Jonathan Thorn, Kansas City, MO (US); Russell Heinen, Kansas City, MO (US)

(73) Assignee: Schenck Process LLC, Kansas City, MO (US)

( * ) Notice: Subject to any disclaimer, the term of this patent is extended or adjusted under 35 U.S.C. 154(b) by 54 days.

(21) Appl. No.: 14/855,577

(22) Filed: Sep. 16, 2015

(65) Prior Publication Data

US 2016/0089463 A1 Mar. 31, 2016

Related U.S. Application Data

(60) Provisional application No. 62/057,020, filed on Sep. 29, 2014.

(51) Int. Cl.
*A61L 2/20* (2006.01)

(52) U.S. Cl.
CPC .......... *A61L 2/202* (2013.01); *B65G 2207/26* (2013.01)

(58) Field of Classification Search
CPC ........................... A61L 2/202; B65G 2207/26
USPC ......................................................... 422/29
See application file for complete search history.

(56) References Cited

U.S. PATENT DOCUMENTS

| 8,071,526 B2 * | 12/2011 | Lynn | ................... B01F 3/04475 210/758 |
| 2001/0017303 A1 * | 8/2001 | McKenzie | ............. B65D 88/28 222/181.1 |
| 2003/0124039 A1 | 7/2003 | Ryan et al. | |
| 2003/0129111 A1 | 7/2003 | Miller et al. | |

(Continued)

FOREIGN PATENT DOCUMENTS

| BE | 463229 | 2/1946 |
| CN | 2516164 | 10/2002 |

(Continued)

OTHER PUBLICATIONS

European Search Report for EP3000484, dated Jun. 1, 2016, 13 pages.

(Continued)

*Primary Examiner* — Kevin Joyner
(74) *Attorney, Agent, or Firm* — Hovey Williams LLP

(57) ABSTRACT

A sanitization system for sanitizing a convey line broadly includes an ozone generation and delivery module, a compressed air source, and an air flow control system, and an ozone measurement and destruction module. The ozone generation and delivery module includes ozone generator, an ozone flow meter, a first ozone analyzer, a humidifier, and a humidity sensor and introduces a measured ozone gas stream into the convey line so that the ozone disinfects the inner surfaces of the convey line. The humidifier introduces moisture into the convey line to increase the effectiveness of the ozone as a disinfection agent. The ozone measurement and destruction module includes a second ozone analyzer, an ozone destructor, and an ozone monitor and removes ozone from the gas stream. The ozone measurement and destruction module also ensures that a desired amount of ozone reaches the end of the convey line.

19 Claims, 2 Drawing Sheets

(56) References Cited

U.S. PATENT DOCUMENTS

Figure 1:
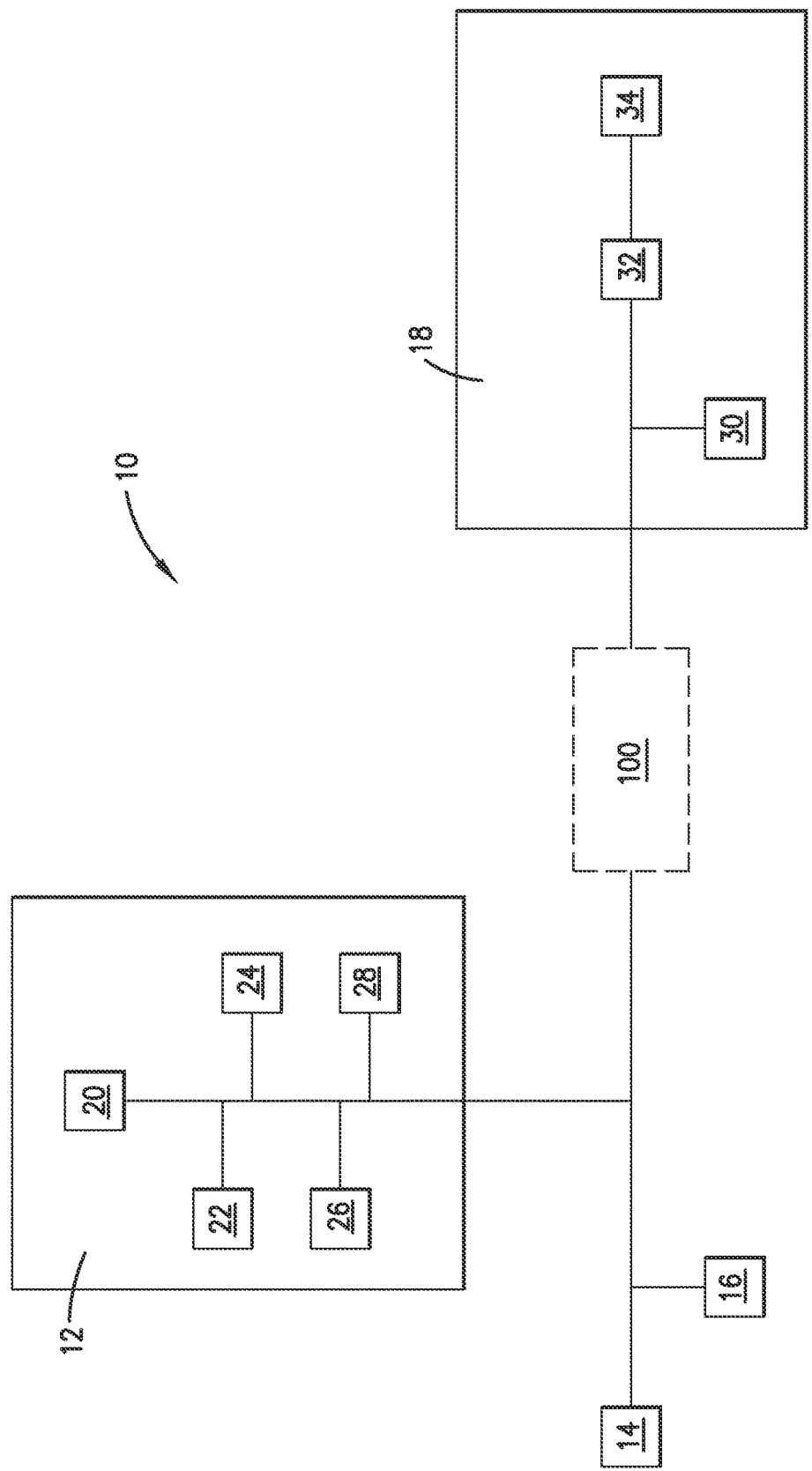

2007/0280867 A1    12/2007  Miller et al.
2009/0191091 A1*  7/2009  Danchenko ............ A23B 9/025
                                                      422/32
2011/0252983 A1*  10/2011  Pacheco Da Cunha ....................
                                                      A23B 9/18
                                                      99/477
2015/0024096 A1*  1/2015  Leech ....................... A23L 3/28
                                                      426/248

FOREIGN PATENT DOCUMENTS

| CN | 203493952   | 3/2014  |
|----|-------------|---------|
| JP | 2004222846  | 8/2004  |
| WO | 99/39723    | 8/1999  |
| WO | 2006/028457 | 3/2006  |
| WO | 2011/143082 | 11/2011 |

OTHER PUBLICATIONS

"Validation of Ozone as a Sanitizing Agent in Pneumatic Conveying Pipelines" by Thorn, Jonathan, M.S., Schenck Process, presented Apr. 2015 at Petfood Forum USA, retrieved on Jan. 29, 2016, http://petfoodforum.niu.edu/petfood/docs/Thorn-Validating-Ozone-as-Sanitizing-Agent.pdf, 36 pages.

* cited by examiner

METHOD AND SYSTEM FOR CLEANING AND SANITIZING CONVEY LINES

RELATED APPLICATIONS

This patent application is a non-provisional patent application claiming priority benefit with regard to all common subject matter of U.S. Provisional Patent Application No. 62/057,020, filed Sep. 29, 2014, and entitled "METHOD AND SYSTEM FOR CLEANING AND SANITIZING CONVEY LINES". The provisional patent application is hereby incorporated by reference in its entirety into the present application.

BACKGROUND

The present invention relates to systems and methods for sanitizing material conveying systems. More particularly, the present invention relates to a sanitization system and method for sanitizing a convey line for a particulate material or other small matter convey line via an ozone gas stream released through the convey line.

Pneumatic conveying systems use air, inert gas, or other similar medium to move large quantities of particulate material or other small matter through a material conveying pipe or other conduit (referred to herein as a "convey line"). The particulate material may include granular, powder, or pelletized material such as pellets formed of plastic material or other chemicals, bulk commodity grains and feed material, soap powders, and other similar bulk materials.

Some convey lines must be periodically cleaned and sanitized to remove and/or prevent the growth of unwanted bacteria on their inner surfaces. However, convey lines are typically semi-permanently installed and cannot be easily removed for cleaning. Convey lines are therefore typically cleaned and sanitized in place. The cleaning medium must also be easily removed so as to not create another form of contamination in the convey lines. Unfortunately, cleaning mediums that kill bacteria are typically wet processes and are not easily removed from convey lines, while cleaning mediums that are easily removed form convey lines do little to kill bacteria.

SUMMARY

The present invention solves the above-described problems and provides a distinct advance in the art of convey line sanitization systems. More particularly, the present invention provides a sanitization system that sanitizes a convey line with a medium that effectively kills bacteria in the convey line and that is relatively easy to remove from the convey line after sanitizing the convey line.

An embodiment of the sanitization system sanitizes convey lines via an ozone gas or air stream and broadly includes an ozone generation and delivery module, a compressed air source, an air flow control system, and an ozone measurement and destruction module.

The ozone generation and delivery module produces ozone and introduces it into the convey line. An embodiment of the ozone generation and delivery module broadly includes an ozone generator, an ozone flow meter, a first ozone analyzer, a humidifier, and a humidity sensor.

The ozone generator concentrates atmospheric oxygen or oxygen from an oxygen supply and converts it to ozone. Alternatively, the ozone may be supplied to the sanitization system from an external source.

The ozone flow meter controls the amount of ozone delivered to the convey line. The ozone flow meter may be manually or automatically controlled and/or monitored.

The first ozone analyzer measures the concentration of ozone delivered to the convey line. The first ozone analyzer may be communicatively coupled with the ozone flow meter via a controller for changing the amount of ozone delivered to the convey line according to the concentration of ozone measured by the first ozone analyzer.

The humidity sensor senses the amount of moisture in the ozone gas stream. The humidity sensor may be communicatively coupled with the humidifier via a controller for changing the amount of moisture added to the ozone gas stream according to the amount of moisture sensed by the humidity sensor.

The compressed air source provides pressurized air for release into the convey line. The compressed air source may include pressure tanks, pumps, valves, and other compressed air dispensing components.

The air flow control system controls the amount of pressured air introduced into the convey line for carrying ozone through the convey line. The air flow control system may include valves, computer controls and other air flow control components.

The ozone measurement and destruction module measures the ozone level at the end of the convey line and captures most of the remaining ozone so that the stream of gas exiting the convey line can be safely returned to the atmosphere. An embodiment of the ozone measurement and destruction module broadly includes a second ozone analyzer, an ozone destructor, and an ozone monitor.

The second ozone analyzer measures the concentration of ozone at the end of the convey line to verify that the desired levels of ozone were achieved and maintained in the convey line. The second ozone analyzer may be communicatively coupled with the ozone generation and delivery module via a controller to change the amount of ozone being introduced to the convey line according to the amount of ozone measured by the second ozone analyzer.

The ozone destructor converts the ozone at the end of the convey line back into. The ozone destructor may be rated to meet local or national air quality and safety requirements or more stringent industry standards. The ozone monitor senses the amount of ozone remaining in the gas or air stream in the convey line or removed from the gas or air stream so as to ensure that a sufficient amount of ozone was removed.

Operation of the sanitization system will now be summarized. First, the convey line may be disconnected from the hopper or surge bin before cleaning and/or sanitization. The convey line may then be cleaned via "pigging", "dry ice conveying", or any other conventional cleaning process so as to remove residual build-up of particulate material.

The ozone generator may then convert atmospheric oxygen or compressed oxygen into ozone. The compressed air source and air flow control system may then release a measured air or gas stream into the convey line at a desired rate and dwell time. The ozone generation and delivery module may then release the ozone into the gas stream. Alternatively, the ozone may be released into the gas stream before the gas enters the convey line. The first ozone analyzer may then sense ozone flowing into the convey line and the controller may instruct the ozone flow meter to increase or decrease the amount of ozone being released into the gas stream accordingly. The humidifier may then add moisture to the gas stream according to the current level of moisture sensed by the humidity sensor. The second ozone analyzer may then measure the amount of ozone reaching the end or a downstream portion of the convey line and a controller may then instruct the ozone generation and delivery module to increase or decrease the amount of ozone being released into the gas stream accordingly.

The ozone destructor may capture most of the remaining ozone and convert it to oxygen or otherwise chemically modify the ozone so that the stream of gas exiting the convey line can be safely returned to the atmosphere. The ozone monitor may then sense the amount of ozone remaining in the gas or air stream in the convey line or removed from the gas or air stream so as to ensure that a sufficient amount of ozone was removed.

The above-described sanitization system provides several advantages over conventional systems. For example, the sanitization system significantly reduces the amount of *E-coli, Salmonella*, and *Listeria* on the interior pipe wall of the convey line and other metal surfaces. Ozone as a sanitization agent is ideal for material handling convey lines because no drying is required and any residual ozone remaining in the gas or air stream will dissipate back into the atmosphere and become oxygen. In addition, the effectiveness of ozone as a sanitizing agent increases dramatically in the presence of moisture provided by the humidifier.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Figure 2:
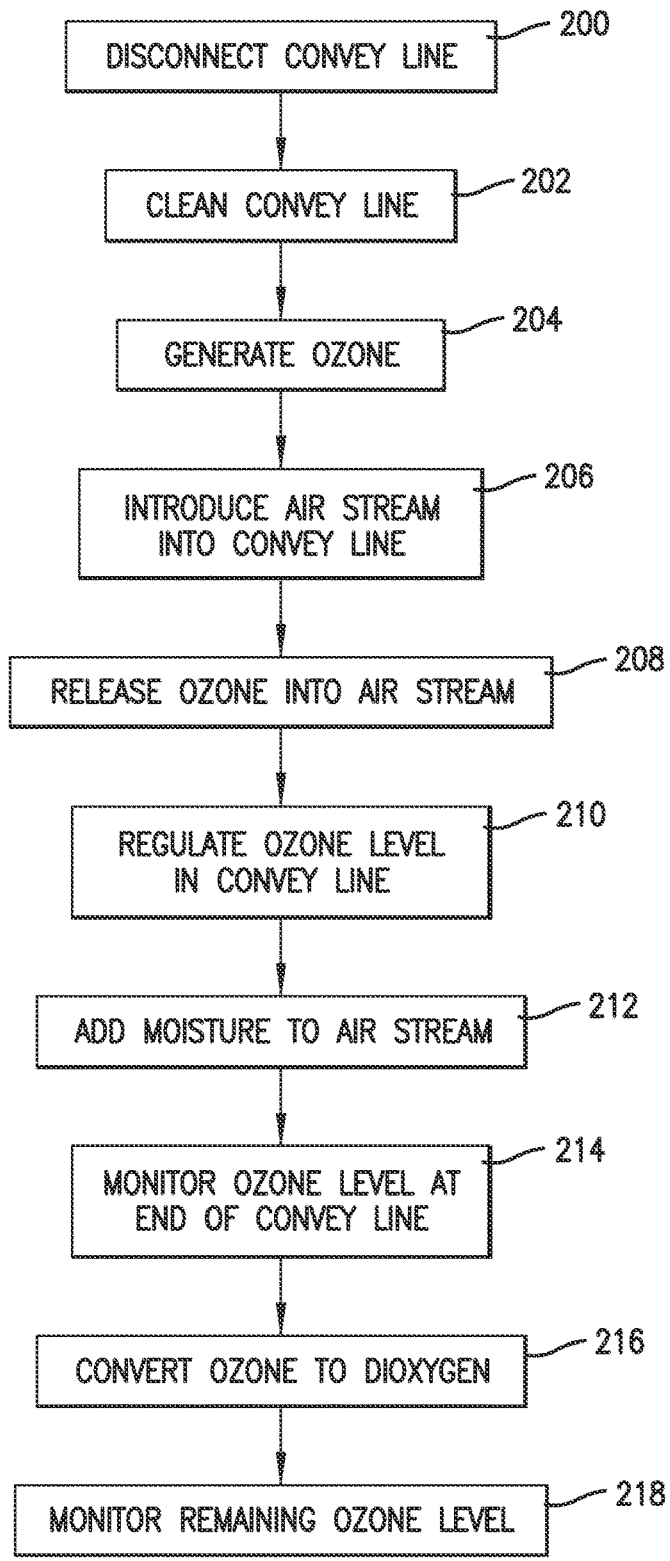

Embodiments of the present invention are described in detail below with reference to the attached drawing figures, wherein:

FIG. 1 is a schematic diagram of a sanitization system constructed in accordance with an embodiment of the present invention; and FIG. 2 is a flow diagram depicting steps in a method of using the sanitization system of FIG. 1 to sanitize a convey line.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning now to FIG. 1, a convey line sanitization system 10 constructed in accordance with an embodiment of the invention is illustrated. The sanitization system 10 may be used to clean and sanitize any convey line including those used for moving particulate material including granular, powder, or pelletized material such as plastic pellets, bulk commodity grains and feed material, soap powders, and any other particulate material. The sanitization system 10 broadly comprises an ozone generation and delivery module 12, a compressed air source 14, an air flow control system 16, and an ozone measurement and destruction module 18.

The ozone generation and delivery module 12 produces ozone and introduces it into a convey line 100. The ozone generation and delivery module 12 broadly includes an ozone generator 20, an ozone flow meter 22, a first ozone analyzer 24, a humidifier 26, and a humidity sensor 28.

The ozone generator 20 concentrates atmospheric oxygen or oxygen from an oxygen supply and converts it to ozone. The ozone generator 20 may be any conventional ozone generator or generation system. Alternatively, the ozone may be supplied to the sanitization system 10 from an external source.

The ozone flow meter 22 controls the amount of ozone delivered to the convey line 100 and may be any conventional flow metering device or system. The ozone flow meter 22 may be manually or automatically controlled and/or monitored.

The first ozone analyzer 24 measures the concentration of ozone delivered to the convey line 100 and may be any conventional ozone analyzer. The first ozone analyzer 24 may be communicatively coupled with the ozone flow meter 22 via a controller for changing the amount of ozone delivered to the convey line 100 according to the concentration of ozone measured by the first ozone analyzer 24. The ozone flow meter 22 and first ozone analyzer 24 may ensure that the gas stream comprises 1800 ppm of ozone or any other suitable concentration level.

The humidifier 26 adds moisture to the ozone and may be any conventional humidifier or humidifier system. Applicant has discovered that the presence of moisture dramatically increases the effectiveness of ozone as a sanitizing agent. In one embodiment, the humidifier 26 may introduce moisture in the ozone gas stream such that the ozone gas stream has an 85% or greater relative humidity.

The humidity sensor 28 senses the amount of moisture in the ozone gas stream and may be any conventional capacitive or similar sensor. The humidity sensor 28 may be communicatively coupled with the humidifier 26 via a controller for changing the amount of moisture added to the ozone gas stream according to the amount of moisture sensed by the humidity sensor 28.

The compressed air source 14 provides pressurized air for release into the convey line 100 and may be a pressure blower or any other conventional compressed air source.

The compressed air source 14 may include pressure tanks, pumps, valves, and other compressed air dispensing components.

The air flow control system 16 controls the amount of pressured air introduced into the convey line 100 for carrying ozone through the convey line 100 and may be any conventional air flow control system such as a Mac Process E-Finity air management control system having a Macturi venturi valve and PLC controls. Alternatively, the pressurized air may be controlled locally with the ozone generation by a dedicated flow control valve.

The ozone measurement and destruction module 18 measures the ozone level at the end of the convey line 100 and captures most of the remaining ozone so that the stream of gas exiting the convey line 100 can be safely returned to the atmosphere. The ozone measurement and destruction module 18 broadly includes a second ozone analyzer 30, an ozone destructor 32, and an ozone monitor 34.

The second ozone analyzer 30 measures the concentration of ozone at the end of the convey line 100 to verify that the desired levels of ozone were achieved and maintained in the convey line 100. The second ozone analyzer 30 may be any conventional ozone analyzer and may be the same type and/or model as the first ozone analyzer 24. The second ozone analyzer 30 may be communicatively coupled with the ozone generation and delivery module 18 via a controller to change the amount of ozone being introduced to the convey line 100 according to the amount of ozone measured by the second ozone analyzer.

The ozone destructor 32 converts the ozone at the end of the convey line 100 back into oxygen and may be any conventional ozone destructor such as a thermal or carbon-based ozone destructor. The ozone destructor 32 may be rated to meet local or national air quality requirements or more stringent air quality and safety requirements.

The ozone monitor 34 senses the amount of ozone remaining in the gas or air stream in the convey line or removed from the gas or air stream so as to ensure that a sufficient amount of ozone was removed. The ozone monitor 34 may be any conventional ozone sensor.

Operation of the sanitization system 10 will now be described in more detail. First, the convey line 100 may be disconnected from a hopper or surge bin before cleaning and/or sanitization, as shown in block 200 of FIG. 2.

The convey line 100 may then be cleaned via "pigging", "dry ice conveying", or any other conventional cleaning process so as to remove residual build-up of particulate matter, as shown in block 202.

The ozone generator 20 may then convert atmospheric oxygen or compressed oxygen into ozone, as shown in block 204.

The compressed air source 14 and air flow control system 16 may then release a measured air or gas stream into the convey line 100 at a desired rate and dwell time, as shown in block 206.

The ozone generation and delivery module 12 may then release the ozone into the gas stream, as shown in block 208. Alternatively, the ozone may be released into the gas stream before the gas enters the convey line 100.

The first ozone analyzer 24 may then sense ozone flowing into the convey line and the controller may instruct the ozone flow meter 22 to increase or decrease the amount of ozone being released into the gas stream accordingly, as shown in block 210. For example, if the desired ozone level is 1800 ppm, the controller may instruct the ozone flow meter 22 to increase the amount of ozone if the current ozone level is 1750 ppm and decrease the amount of ozone if the current ozone level is 1900 ppm.

The humidifier 26 may then add moisture to the gas stream according to the current level of moisture sensed by the humidity sensor 28, as shown in block 212. For example, if the target relative humidity level is 85%, the humidifier may increase the amount of moisture if the current relative humidity level is 80% and decrease the amount of moisture if the current relative humidity level is 90%.

The second ozone analyzer 30 may then measure the amount of ozone reaching the end or a downstream portion of the convey line 100 and a controller may then instruct the ozone generation and delivery module 12 to increase or decrease the amount of ozone being released into the gas stream accordingly, as shown in block 214.

The ozone destructor 32 may then capture most of the remaining ozone and convert it to oxygen or otherwise chemically modify the ozone so that the stream of gas exiting the convey line 100 can be safely returned to the atmosphere, as shown in block 216.

The ozone monitor 34 may then sense the amount of ozone remaining in the gas or air stream in the convey line 100 or removed from the gas or air stream so as to ensure that a sufficient amount of ozone was removed, as shown in block 218.

The sanitization system 10 may treat the convey line 100 as described above for approximately 6 hours to reduce biological contaminates in the convey line 100 from 2-3 log to effectively zero. The gas or air stream velocity may be relatively low so that concentration of ozone in the convey line 100 can be increased with a reduced size ozone generator 20. Applicant has discovered that reduction of the gas or air stream velocity increases dwell time of ozone in the convey line 100 such that ozone takes 5-15 minutes to reach the end of the convey line 100. In one embodiment, the compressed air source 14 and air flow control system 16 may provide an air velocity of approximately 50 fpm. Other flow rates may be desirable depending on the size, complexity, and contamination level of the convey line 100 and other factors. Sanitization is more effectively achieved if the convey line 100 has no ledges or other surfaces that may trap and hold particulate matter. For example, the sanitization system 10 may be more effective if the convey line 100 has machined couplings such as Mac No-Ledge couplings employed at all pipe joints in the convey line. Applicant has further discovered that flow of the gas stream can be manipulated to create flow patterns that cause the ozone to contact or flow near the pipe wall of the convey line, thus increasing the number of contaminants killed or removed from the pipe wall of the convey line. For example, flow velocity of the gas stream may be increased until the gas stream has a turbulent flow pattern.

The above-described sanitization system 10 provides several advantages over conventional systems. For example, the sanitization system 10 can sanitize convey lines from 2-3 log count to below a detectable level. The ozone is ideal for material handling convey lines because no drying is required and any residual ozone remaining in the gas or air stream will dissipate back into the atmosphere and become oxygen. The sanitization system 10 significantly reduces the amount of *E-coli*, *Salmonella*, and *Listeria* on the interior pipe wall of convey lines and other metal surfaces. In addition, the effectiveness of ozone as a sanitizing agent increases dramatically in the presence of moisture provided by the humidifier.

Although the invention has been described with reference to the embodiments illustrated in the attached drawing

Having thus described various embodiments of the invention, what is claimed as new and desired to be protected by Letters Patent includes the following:

1. A sanitization system for sanitizing a convey line including a first end and a second end, wherein the convey line is used to convey particulate material, the sanitizing system comprising:
a cleaning system configured to remove residual build-up of particulate material within the convey line, wherein said cleaning system comprises a pigging system;
an air source configured to generate a stream of air and release the stream of air into the first end of the convey line; and
an ozone generation and delivery module configured to inject ozone into the air stream,
wherein the ozone generation and delivery module includes a humidifier configured to inject moisture into the air stream,
wherein a combination of ozone and moisture injected into the air stream is configured to kill and/or remove contaminants from the convey line.

2. The sanitization system of claim 1, wherein the air source is a compressed air source, the sanitization system further comprising:
an air flow control system configured to regulate an air pressure and flow rate of the air stream flowing through the convey line.

3. The sanitization system of claim 2, wherein the compressed air source and air flow control system generate and maintain an air flow velocity in the convey line of approximately 50 fpm for carrying the ozone through the convey line.

4. The sanitization system of claim 1, wherein the ozone generation and delivery module includes:
an ozone generator configured to convert oxygen into ozone;
an ozone flow meter configured to control an amount of ozone delivered to the convey line;
a first ozone analyzer configured to measure a concentration of ozone delivered to the convey line; and
a humidity sensor configured to sense an amount of moisture entering the convey line.

5. The sanitization system of claim 4, wherein the ozone generation and delivery module is configured to produce an ozone air stream in the convey line with 85% relative humidity or greater.

6. The sanitization system of claim 4, wherein the ozone generation and delivery module is configured to produce an ozone air stream in the convey line with approximately 1800 ppm of ozone.

7. A sanitization system for sanitizing a convey line including a first end and a second end, the sanitizing system comprising:
an air source configured to generate a stream of air and release the stream of air into the first end of the convey line;
an ozone generation and delivery module configured to inject ozone into the air stream, wherein the ozone generation and delivery module includes:
an ozone generator configured to convert oxygen into ozone,
an ozone flow meter configured to control an amount of ozone delivered to the convey line,
a first ozone analyzer configured to measure a concentration of ozone delivered to the convey line,
a humidifier configured to add moisture into the convey line, and
a humidity sensor configured to sense an amount of moisture entering the convey line,
wherein a combination of ozone and moisture injected into the air stream is configured to kill and/or remove contaminants from the convey line; and
an ozone measurement and destruction module including:
a second ozone analyzer configured to sense an amount of ozone remaining in the convey line after ozone is removed from the convey line,
an ozone destructor configured to remove ozone from the convey line,
an ozone monitor configured to sense an amount of ozone being removed from the convey line.

8. A method of sanitizing a convey line having an inner wall, a first end, and a second end, wherein the convey line is used to convey particulate material, the method comprising the steps of:
cleaning the convey line by removing residual build-up of particulate material within the convey line, wherein said cleaning step is performed by a pigging process;
releasing an air stream into the first end of the convey line;
injecting ozone into the air stream;
injecting moisture into the air stream, wherein a combination of ozone and moisture injected into the air stream kills and/or removes contaminants from the convey line; and
removing ozone remaining in the air stream from the second end of the convey line.

9. The method of claim 8, further comprising the step of regulating an air velocity of the air stream to approximately 50 fpm.

10. The method of claim 8, wherein the moisture is injected into the air stream such that the air stream has 85% or greater relative humidity.

11. The method of claim 8, further comprising the step of controlling a dwell time of the ozone in the convey line.

12. The method of claim 8, further comprising the step of regulating a concentration of ozone in the convey line by controlling the amount of ozone being injected into the convey line.

13. The method of claim 8, further comprising the step of regulating a concentration of the ozone in the convey line by controlling an amount and pressure of compressed air being injected into the convey line.

14. The method of claim 8, wherein the ozone is injected into the air stream such that the air stream has approximately 1800 ppm of ozone.

15. The method of claim 8, further comprising the step of verifying that a desired ozone level was achieved and maintained in the convey line.

16. The method of claim 8, further comprising the step of disconnecting the convey line from a hopper and/or surge bin before injecting the ozone into the air stream.

17. The method of claim 8, further comprising the step of treating the convey line with ozone for at approximately 6 hours.

18. The method of claim 8, further comprising the step of creating a flow pattern in the air stream that increases chances of the ozone flowing near or contacting the inner wall of the convey line so as to increase the interaction between the ozone and the contaminants.

19. A method of sanitizing a convey line having a first end and a second end, the method comprising the steps of:

disconnecting the convey line from a hopper and/or surge bin;
cleaning the convey line by removing residual build-up of particulate matter in the convey line;
providing ozone via an ozone generation and delivery module;
injecting a stream of compressed gas into the first end of the convey line;
injecting the ozone into the gas stream at approximately 1800 ppm of ozone and approximately 50 fpm into the first end of the convey line for approximately 6 hours such that the ozone kills and/or removes contaminants from the convey line;
controlling the dwell time of the ozone in the convey line;
regulating a concentration of the ozone in the convey line by controlling an amount and pressure of compressed gas being injected into the first end of the convey line;
injecting water vapor into the gas stream at 85% or greater humidity so as to increase the sanitizing effects of the ozone;
removing ozone remaining in the gas stream at the second end of the convey line via an ozone destructor; and
reconnecting the convey line to the hopper and/or surge bin.

* * * * *